United States Patent
Hsu et al.

(10) Patent No.: US 7,029,764 B2
(45) Date of Patent: Apr. 18, 2006

(54) ORGANIC ELECTROLUMINESCENT MATERIAL AND ELECTROLUMINESCENT DEVICE BY USING THE SAME

(75) Inventors: Hsiang Lun Hsu, Miaoli (TW); Man-kit Leung, Taipei (TW); Shen-shen Wang, Junghe (TW)

(73) Assignee: RiTdisplay Corporation, Hsinchu (TW)

( * ) Notice: Subject to any disclaimer, the term of this patent is extended or adjusted under 35 U.S.C. 154(b) by 84 days.

(21) Appl. No.: 10/350,007

(22) Filed: Jan. 24, 2003

(65) Prior Publication Data

US 2004/0146742 A1 Jul. 29, 2004

(51) Int. Cl.
*H05B 33/12* (2006.01)
*C09K 11/06* (2006.01)

(52) U.S. Cl. ............... 428/690; 428/917; 313/503; 313/504; 257/40

(58) Field of Classification Search ........... 428/690, 428/917; 313/503, 504, 506; 257/40, 102; 546/23, 79, 80, 81, 89, 112, 113, 114, 115; 548/416, 427, 428, 429, 440, 452; 252/301.16
See application file for complete search history.

(56) References Cited

U.S. PATENT DOCUMENTS

| | | | | |
|---|---|---|---|---|
| 4,841,009 A * | 6/1989 | Kelsey | ............ | 528/75 |
| 5,121,029 A | 6/1992 | Hosokawa et al. | ......... | 313/504 |
| 5,126,214 A | 6/1992 | Tokailin et al. | ............ | 428/690 |
| 5,130,603 A | 7/1992 | Tokailin et al. | ............ | 313/504 |
| 5,281,489 A * | 1/1994 | Mori et al. | ............... | 428/690 |
| 5,516,577 A | 5/1996 | Matsuura et al. | .......... | 428/212 |
| 5,536,949 A | 7/1996 | Hosokawa et al. | ......... | 257/40 |
| 6,093,864 A | 7/2000 | Tokailin et al. | ............ | 585/25 |
| 6,195,142 B1 * | 2/2001 | Gyotoku et al. | ............ | 349/69 |
| 6,228,514 B1 * | 5/2001 | Tadashi et al. | ............ | 428/690 |
| 6,501,217 B1 * | 12/2002 | Beierlein et al. | ........... | 313/504 |

FOREIGN PATENT DOCUMENTS

EP WO 99/39393 * 8/1999

(Continued)

OTHER PUBLICATIONS

Helfrich et al., "Transients of Volume-Controlled Current and of Recombination Radiation in Anthracene," The Journal of Chemical Physics, vol. 44, No. 3, Apr. 15, 1966, pp. 2902-2909.

(Continued)

*Primary Examiner*—Rena Dye
*Assistant Examiner*—Camie S. Thompson
(74) *Attorney, Agent, or Firm*—Jiang Chyun IP Office

(57) ABSTRACT

An organic electroluminescent material of the formula:

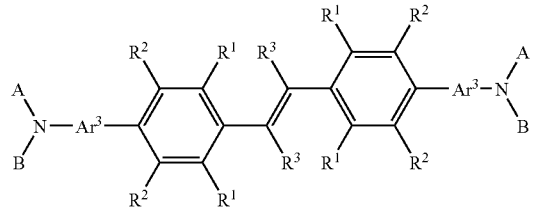

wherein $R^1$, $R^2$ and $R^3$ are selected from the group consisting of hydrogen, halogen, nitryl, alkyl, cycloalkyl, alkyloxy, alkenyl, amine, aryl, polyaryl, arylalkyl, and propenyloxy, $Ar^3$ is at least one selected from the group consisting of aryl and polyaryl and A and B are at least one selected from the group consisting of hydrogen, alkyl, cycloalkyl, alkyloxy, alkenyl, amine, aryl, polyaryl, arylalkyl, and propenyloxy. An electroluminescent device having the organic electroluminescent material is provided.

20 Claims, 2 Drawing Sheets

FOREIGN PATENT DOCUMENTS

JP            11-260551    *    9/1999

OTHER PUBLICATIONS

Vincett et al., "Electrical Conduction and Low Voltage Blue Electroluminescence in Vacuum-Deposited Organic Films," Thin Solid Films, vol. 94, 1982, pp. 171-183.

Tang et al., "Organic electroluminescent diodes," Appl. Phys. Lett, vol. 51, No. 12, Sep. 21, 1987, pp. 913-915.

Behnisch et al., "Synthesis of new 1,3,5-tris-styryl-benzene compounds with tunable photo- and electroluminescent properties," Synthetic Metals, vol. 121, 2001, pp. 1661-1662.

Kim et al., "Synthesis and characterization of star-shaped organic light emitting materials containing long alkyl chain," Synthetic Metals, vol. 121, 2001, pp. 1665-1666.

Hosokawa et al., "Highly efficient blue eletroluminescence from a distyrylarylene emitting layer with a new dopant," Appl. Phys. Lett., vol. 67, No. 26, Dec. 25, 1995, pp. 3853-3855.

Kwok et al., "Synthesis and characterization of blue-emitting, distyrylstilbenes bearing electron affinitive dendrons," Materials Science and Engineering, vol. B85, 2001, pp. 126-130.

* cited by examiner

ORGANIC ELECTROLUMINESCENT MATERIAL AND ELECTROLUMINESCENT DEVICE BY USING THE SAME

BACKGROUND OF THE INVENTION

1. Field of Invention

This invention relates to a luminescent material and device and, more particular, to an organic electroluminescent (OEL) material and an OEL device.

2. Related Art

Following the advances in electrical technology, light and high efficiency displays, such as liquid crystal displays (LCD), are well developed. However, the LCD has several drawbacks: the narrow viewing angle, the response time which is not fast enough to display high-speed animation, and the increased power requirement for driving the panel. Moreover, a large panel cannot be easily manufactured in LCD structures.

Compared to the LCD, organic light-emitting diodes are self-emissive, have a full viewing angle, are high power efficient, are easily manufactured, are low cost, have a fast response time, and are full color. Therefore, organic light-emitting diodes could be the major flat display and light source, including being used as special light sources and for normal illumination, in the future.

Referring to FIG. 1, an organic light-emitting diode 1 includes a substrate II, a first electrode 12, an organic EL layer 13, and a second electrode 14. When applying a direct current to the diode 1, holes are injected from the first electrode 12 into the organic EL layer 13 while electrons are injected from the second electrode 14. Based on the applied voltage, the holes and electrons are moved in the organic EL layer 13, and are combined to generate excitons. The excitons can excite organic EL materials of the organic EL layer 13, so that the excited organic EL materials emit light to release energy.

Those skilled in the art should know that organic light-emitting diodes utilize the self-emissive of organic functional materials to achieve the objective of displaying.

The organic compound of the organic EL layer has been long studied. For example, W. Helfrish, Dresmer, Williams, et al. succeeded in emission of blue light using anthracene crystals (J. Chem. Phys., 44, 2902 (1966)). Vincett, Barlow, et al. produced a light emitting device by a vapor deposition method, using a condensed polycyclic aromatic compound (Thin Solid Films, 94, 171 (1982)). However, only a light emitting device low in luminance and luminous efficiency has been obtained.

In 1987, C. W. Tang and S. A. Van Slyke disclosed an organic EL layer structure having an organic thin film and a transporting thin film. The transporting thin film is a hole transporting layer or an electron transporting layer. It is reported that the maximum luminance provided is more than 1,000 cd/m² and an efficiency of 1 lm/W (Appl. Phys. Lett., Vol. 51, 913 (1987)).

After that, scientists developed another organic EL layer structure having three layers to decrease driving voltage of the diode and to increase the maximum luminescence. In this case, the organic EL layer structure having a luminescent layer, a hole transporting layer, and an electron transporting layer.

It is also reported that a distyrylbenzene compound well known as laser dye exhibits high fluorescent properties in the region of blue to blue green, and a light emitting material using the distyrylbenzene compound in a single layer form emits EL light of about 80 cd/m² (European Patent 0319881). In the recent 10 years, Idemitsu Kosan Co. disclosed derivatives of distyrylbenzene compounds and has many granted patents such as U.S. Pat. Nos. 5,121,029, 5,126,214, 5,130,603, 5,516,577, 5,536,949, 6,093,864, WO 02/20459, and et al. In addition, the styrylbenzene compound and its derivatives are reported in Synthetic Metal 121 (2001) 1661, Synthetic Metal 121 (2001) 1665, Appl. Phys. Lett. 67 (26) 1995, Materials Science, and Engineering B85 (2001) 126.

Although derivatives of distyrylbenzene compounds are well studied utilizing in organic EL material and organic EL device, there are still several drawbacks such as low luminance and emitting efficiency, high driving voltage, color impurity, and et al. For example, as disclosed in U.S. Pat. No. 5,130,603, N,N'-diphenyl-N,N'-bis-(3-methylphenyl)-[1,1'-biphenyl]-4,4'-diamine (TPD) is used in a hole transporting layer, and 2,5-bis(2,2-di-p-tolyvinyl)xylene (DTVX) is used in a luminescent layer. When applying 5 volts, the luminance of the organic EL device having TPD and DTVX is 300 cd/m², and the luminescent wavelength of the device is 486 nm. When applying 7 volts, the maximum luminance of the organic EL device is 1,000 cd/m². In addition, as disclosed in U.S. Pat. No. 5,536,949, TPD is used in the hole transporting layer, 4,4'-Bis(2,2-diphenylvinyl)biphenyl (DPVBi) is used in the luminescent layer which doped with 4,4'-B is[2-{4-(N,N-diphenylamino)pheny} vinyl]biphenyl (DPAVB i), and 8-hydroxyquinoline is used in the electron transporting layer. In this case, when applying 8 volts, the luminance of the organic EL device is 400 cd/m², and the luminescent wavelength of the device is 494 nm. In U.S. Pat. No. 6,093,864, the organic EL device has similar properties as mentioned above. In this case, derivatives of distyrylbenzene compounds are formed in the organic EL device by the evaporation method. However, these molecules are thermally unstable, so that they could be thermally degraded during the testing of the manufacturing processes.

Alternatively, some scientists have disclosed that tris-styrylbenzene compounds (Synthetic Metal 121 (2001) 1661) or tetrakis-styrylbenzene compounds (Synthetic Metal 121 (2001) 1665) can be used in the luminescent layer. In practice, however, the luminous efficiency of the organic EL device having those compounds is unsatisfactory, and it is difficult and complex to manufacture an organic EL device having those compounds.

Therefore, it is an important objective of the invention to provide an organic EL material and organic EL device that can improve luminance, emitting efficiency, driving voltage, and color impurity. Furthermore, the organic EL material and organic EL device of this invention can also improve thermal stability to prevent thermal degradation.

SUMMARY OF THE INVENTION

In view of the above-mentioned problems, an objective of the current invention is to provide an organic EL material and EL device, which has enhanced luminance and emitting efficiency, lowered driving voltage, increased color purity, and high thermal stability.

To achieve the above objective, the invention provides an organic EL material of the formula (I):

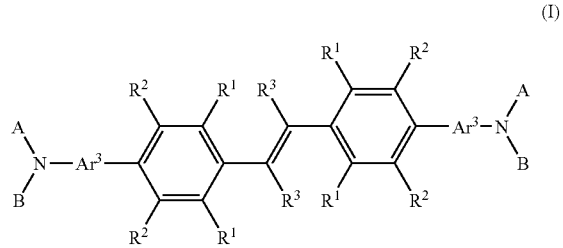

wherein $R^1$, $R^2$ and $R^3$ are at least one selected from the group consisting of hydrogen, halogen, nitryl, alkyl, cycloalkyl, alkyloxy, alkenyl, amine, aryl, polyaryl, arylalkyl, and propenyloxy, $Ar^3$ is at least one selected from the group consisting of aryl and polyaryl, and A and B are at least one selected from the group consisting of hydrogen, alkyl, cycloalkyl, alkyloxy, alkenyl, amine, aryl, polyaryl, arylalkyl, and propenyloxy.

Moreover, this invention also provides an organic EL device, which includes two electrodes and an organic EL layer sandwiched between the electrodes. In this invention, the organic EL layer includes the mentioned organic EL material.

BRIEF DESCRIPTION OF THE DRAWINGS

The invention will become more fully understood from the detailed description given in the herein below illustration only, and thus are not limitative of the present invention, and wherein.

DETAILED DESCRIPTION OF THE INVENTION

Figure 1:
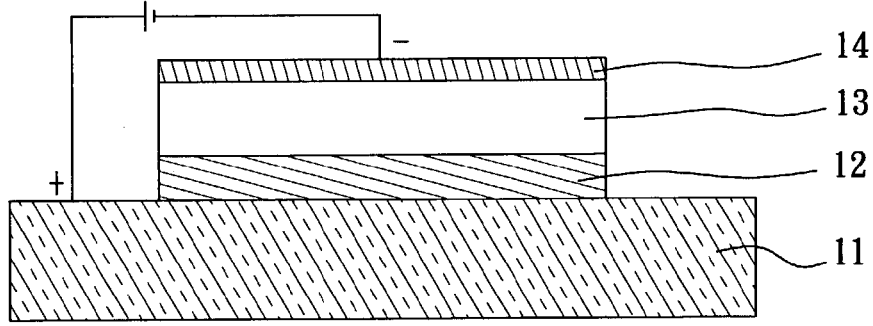
FIG. 1 is a schematic illustration showing a conventional organic light-emitting diode.

The present invention will hereinafter be explained in detail.

In this invention, an organic EL material of the general formula (I):

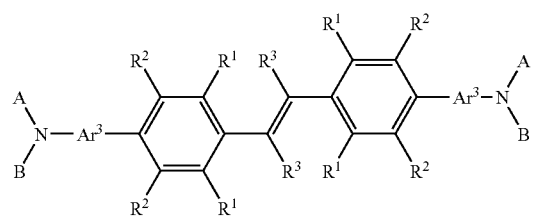

(I)

is used.

In the above general formula (I), $R^1$, $R^2$ and $R^3$ are at least one selected from the group consisting of hydrogen, halogen, nitryl, alkyl, cycloalkyl, alkyloxy, alkenyl, amine, aryl, polyaryl, arylalkyl, and propenyloxy. More specifically, $R^1$, $R^2$ and $R^3$ are at least one selected from the substituted or unsubstituted group consisting of alkyl having 1 to 10 carbon atoms, cycloalkyl having 1 to 10 carbon atoms, alkyloxy having 1 to 10 carbon atoms, alkenyl having 1 to 10 carbon atoms, amine, aryl having 6 to 30 carbon atoms, polyaryl having 6 to 30 carbon atoms, arylalkyl having 6 to 30 carbon atoms, and propenyloxy having 1 to 10 carbon atoms.

$Ar^3$ is an aryl group or a polyaryl group. For example, $Ar^3$ is at least one selected from the substituted or unsubstituted group consisting of aryl having 6 to 30 carbon atoms, and polyaryl having 6 to 30 carbon atoms. In this presented embodiment, representative examples of $Ar^3$ are shown below.

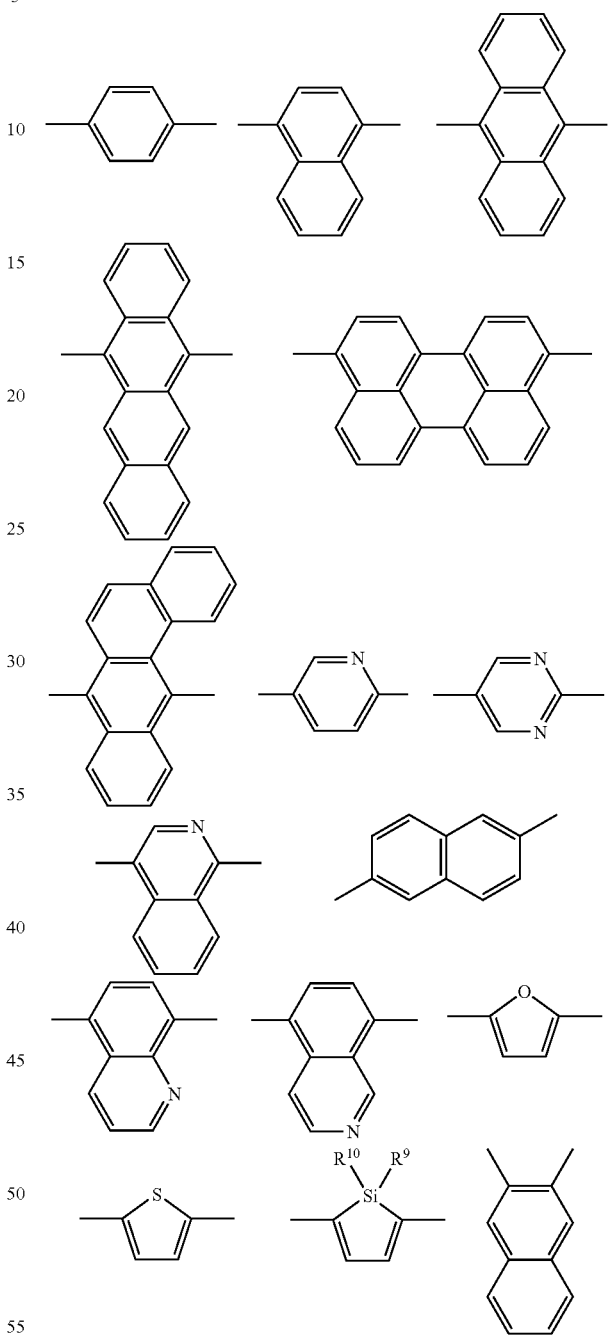

Wherein, $R^9$ and $R^{10}$ are at least one selected from the substituted or unsubstituted group consisting of alkyl having 1 to 10 carbon atoms, aryl having 6 to 30 carbon atoms, polyaryl having 6 to 30 carbon atoms, and arylalkyl having 6 to 30 carbon atoms.

Referring again to general formula (I), A and B are at least one selected from the group consisting of hydrogen, alkyl, cycloalkyl, alkyloxy, alkenyl, amine, aryl, polyaryl, arylalkyl, and propenyloxy. In this presented embodiment, A and B are at least one selected from the substituted or unsubstituted group consisting of alkyl having 1 to 10 carbon atoms, cycloalkyl having 1 to 10 carbon atoms, alkyloxy having 1 to 10 carbon atoms, alkenyl having 1 to 10 carbon atoms, amine, aryl having 6 to 30 carbon atoms, polyaryl having 6 to 30 carbon atoms, arylalkyl having 6 to 30 carbon atoms, and propenyloxy having 1 to 10 carbon atoms.

Moreover, $Ar^3$ could be further bond with A or B. In addition, A and B could be bonded with each other.

As a result, the organic EL material according to the presented embodiment of the invention could be the compound shown below.

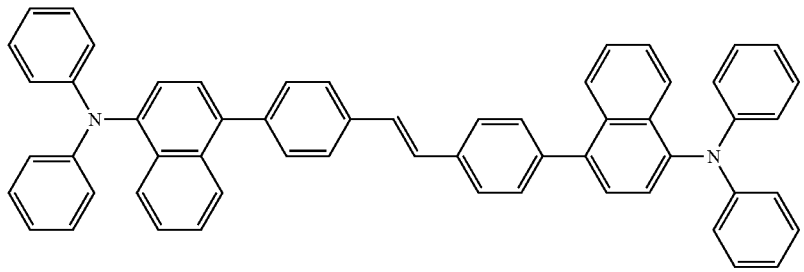

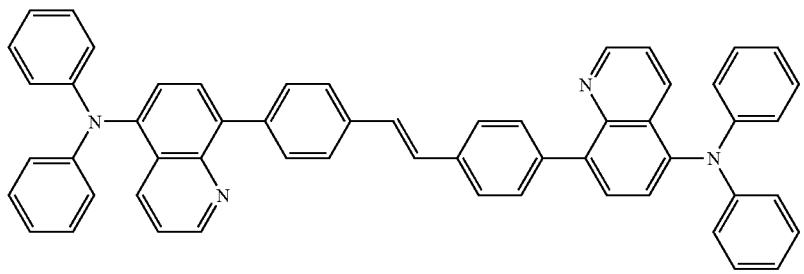

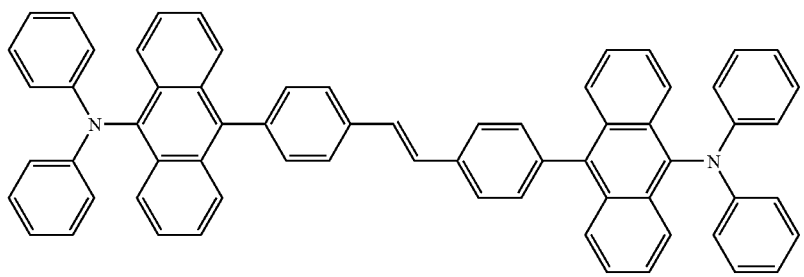

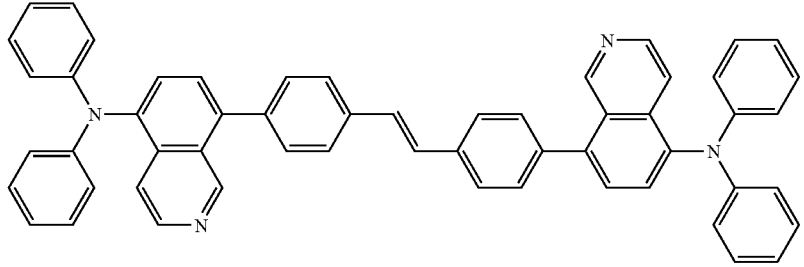

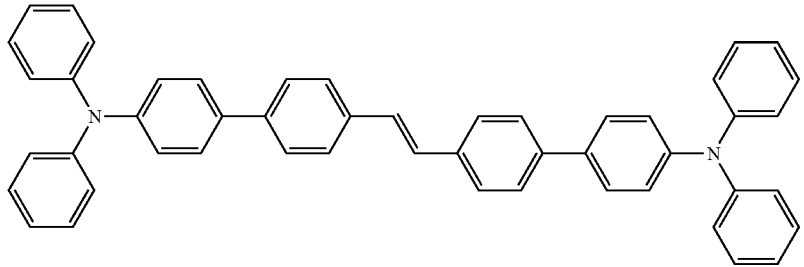

-continued
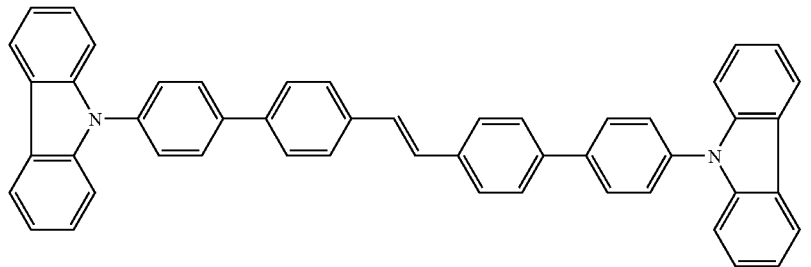
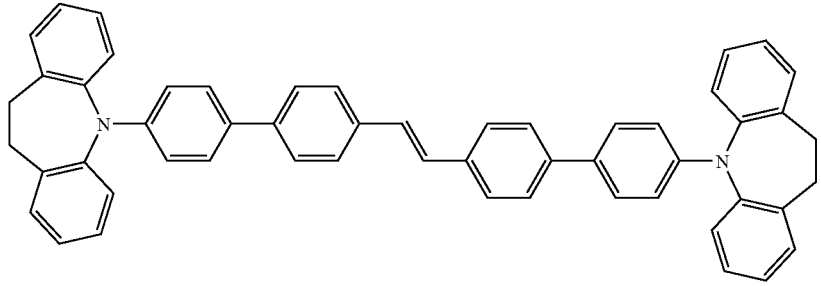
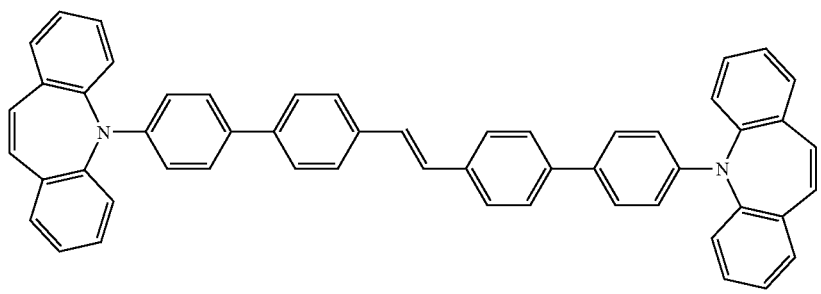
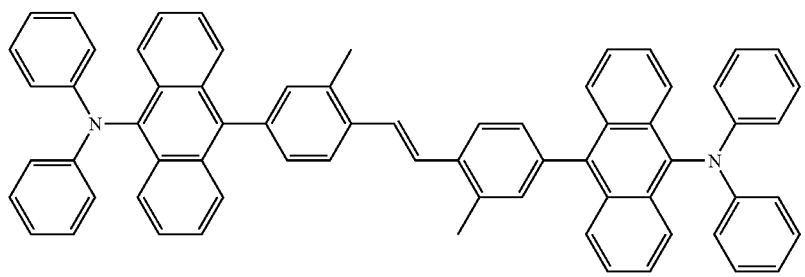
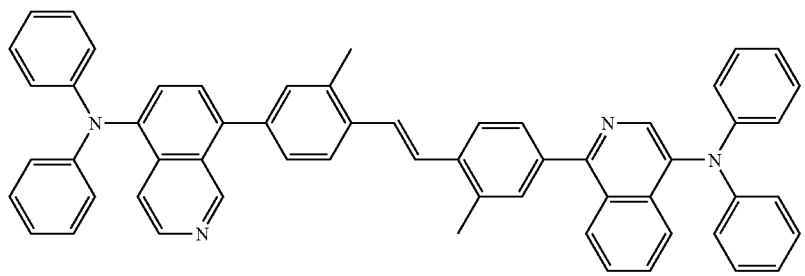
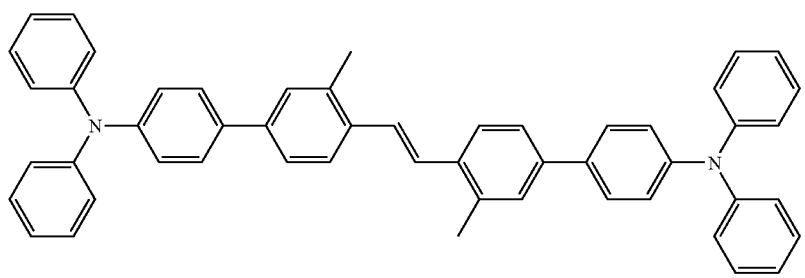

-continued
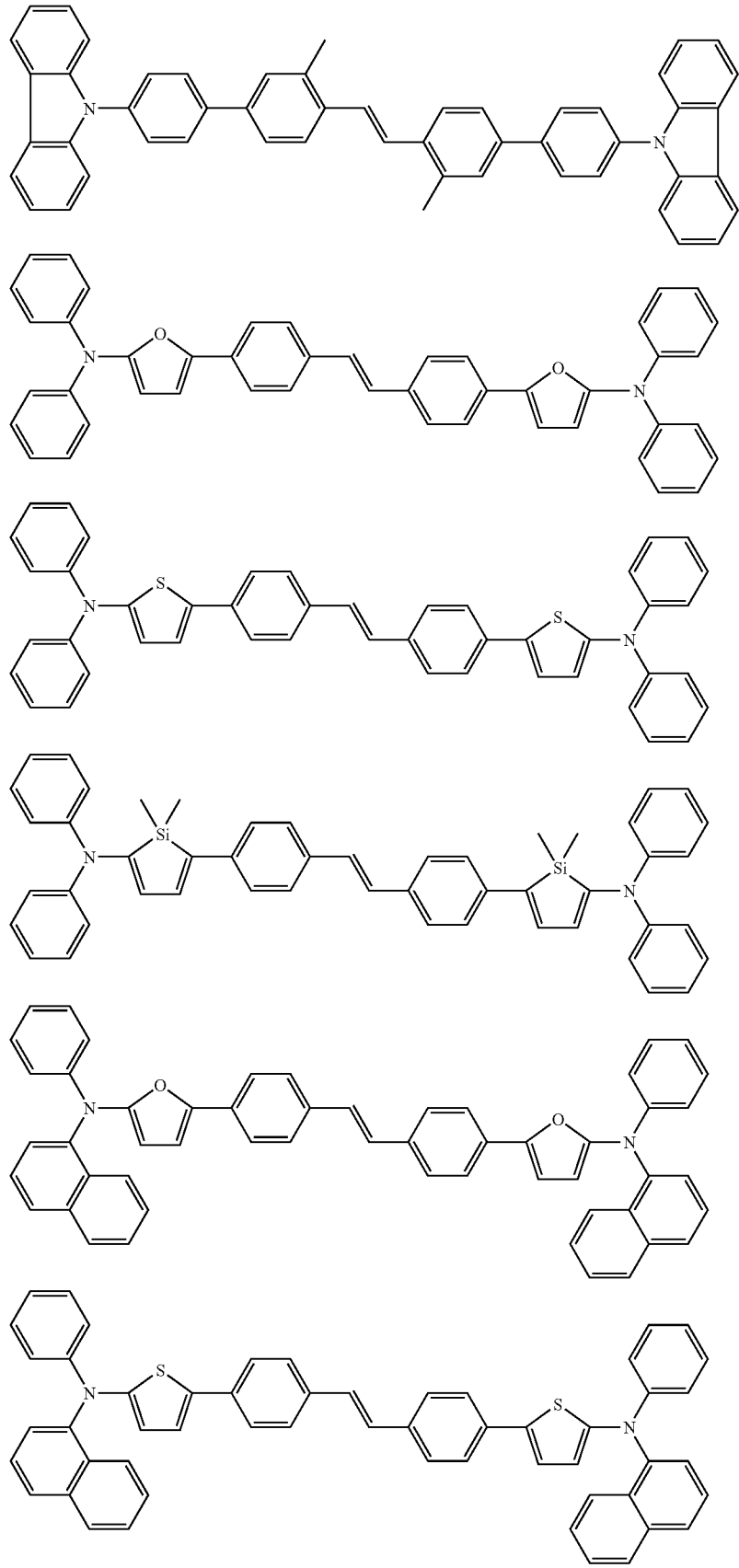

-continued

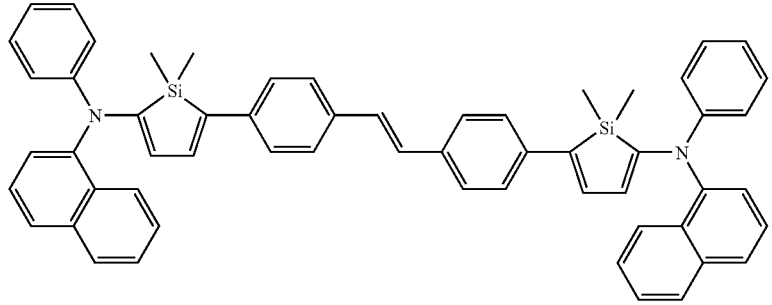

Furthermore, in another embodiment of this invention, the mentioned organic EL material is applied to an organic EL device, including a substrate, a first electrode, an organic EL layer, and a second electrode.

In the embodiment, the first electrode is formed on the substrate, the organic EL layer is formed on the first electrode, and the second electrode is formed on the organic EL layer.

The substrate is a transparent substrate such as a plastic substrate or a flexible substrate. In this embodiment, the plastic substrate or the flexible substrate may be a polycarbonate (PC) substrate or a polyester (PET) substrate.

The first electrode is a transparent anode and is formed on the substrate by utilizing sputtering or ion plating. The first electrode can be made of a conductive metal oxide such as indium-tin oxide (ITO), aluminum-zinc oxide (AZO), or indium-zinc oxide (IZO).

The organic EL layer includes the mentioned organic EL material represented by the general formula (I). In general, the organic EL layer has at least one deposited layer.

Herein below are examples of the structure of the organic EL layer between the anode and the cathode.

(1) anode/luminescent layer/cathode
(2) anode/luminescent layer/electron transporting layer/cathode
(3) anode/hole transporting layer/luminescent layer/cathode
(4) anode/hole transporting layer/luminescent layer/electron transporting layer/cathode
(5) anode hole injecting layer/hole transporting layer/luminescent layer/cathode
(6) anode/hole injecting layer/hole transporting layer/luminescent layer/electron transporting layer/cathode
(7) anode/hole injecting layer/hole transporting layer/luminescent layer/electron transporting layer/electron injecting layer/cathode In the current embodiment, the luminescent layer is composed of the mentioned organic EL material of general formula (I). In addition, the organic EL material can be a dopant of the luminescent layer, and the doping ratio of the organic EL material is greater than 0.01 wt % or less than 10 wt %. The luminescent layer can further include an aryl amino compound substituted with an aryl group or a polyaryl group, an aryl bi-amino compound substituted with an aryl group or a polyaryl group, or an aryl tri-amino compound substituted with an aryl group or a polyaryl group. Therefore, the glass transition temperature of the luminescent layer is higher than 100° C.

Moreover, the mentioned organic EL material of general formula (I) also can be doped in the hole transporting layer of the organic EL layer.

As mentioned above, the hole injecting layer is mainly composed of copper phthalocyanine (CuPc), the hole transporting layer is mainly composed of 4,4'-bis[N-(1-naphthyl)-N-phenylamino]biphenyl (NPB), the electron injecting layer is mainly composed of lithium fluoride (LiF), and the electron transporting layer is mainly composed of tris(8-quinolinato-N1,08)-aluminum (Alq). Each layer of the organic EL layer can be formed upon the first electrode by utilizing evaporation, spin coating, ink jet printing, or printing. In this case, the organic EL material of general formula (I) can be formed by utilizing evaporation, molecular beam evaporation (MBE), immersion, spin coating, casting, bar code, or roll coating.

The second electrode is a cathode and formed by utilizing evaporation, E-gun coating, or sputtering. In the current embodiment, the second electrode is made of aluminum, aluminum/lithium fluoride, calcium, magnesium-silver alloys or silver.

The present invention is described in greater detail with reference to the following examples.

EXAMPLE 1

This example illustrates a synthesis method of the organic EL material according to an embodiment of this invention.

First, 60 g of 4-bromobenzyl bromide and 80 ml of triethyl phosphite are added, and then refluxed for 12 hours while heated at a temperature of 100° C. After that, the solution is distilled at 75° C. under reduced pressure to remove the residual triethyl phosphite, and 70 g of 4-bromobenzyl phosphonic acid ester (95%) is obtained. Next, 2.0 g of 4-bromobenzyl phosphonic acid ester is solved in 70 g of tetrahydrofuran, and 1.32 g of 4-bromobenzaldehyde and 0.65 g of sodium tert-butyoxyl are added into the tetrahydrofuran solution. Then, the solution is refluxed for 6 hours while heated at a temperature of 80° C., so as to retrieve compound (A)(1.87 g, 85%).

In addition, 15 g of triphenylamine dissolved in 50 ml of N,N-dimethylformide is prepared. 11.4 g of N-bromosuccinimide is added into the N,N-dimethylformide solution and the solution is stirred for 12 hours. After 20 ml of water is added, a white crystal is obtained. The white crystal is filtered and dried to obtain 11.70 g of N,N-diphenyl-4-bromoaniline (60%). Next, 8.26 g of N,N-diphenyl-4-bromoaniline is dissolved in 100 ml of tetrahydrofuran. After cooling the solution to −78° C., 24 ml of n-butyl lithium is dropt into the cold solution slowly, then the solution is stirred for 2 hours and the temperature of solution is raised to 0° C. Then, the reacting solution is cooled to −78° C. again, and 5.2 ml of boric acid trimethyl ester is added into the solution slowly. After stirring the reacting solution for 12 hours, 20 ml of 2N HCl is added to terminate the reaction. 100 ml of ethyl ether is used to extract the solution, and the extracted solution is dehydrated by MgSO$_4$. Then, the extracted solution is concentrated, and hexane is added to obtain a white crystal. This white crystal is filtered and dried to obtain 4.3 g of compound (B)(60%).

Then, 1.0 g of compound (A), 2.0 g of compound (B), and 52 mg of [1,1'bis(diphenylphosphino)ferrocene]palladium (II)chloride, which serves as a catalyst, are dissolved in 30 ml of tetrahydrofuran. After heated and refluxed, 10 ml of saturated sodium hydrogencarbonate is added into the solution, and then the solution is heated and refluxed for 12 hours. Then, the solution is cooled to room temperature, and methanol is added to obtain a yellow crystal. This yellow crystal is filtered and dried to produce 2.0 g of compound (C)(96%).

The procedures of synthesis compound (A), compound (B) and compound (C) are shown herebelow:

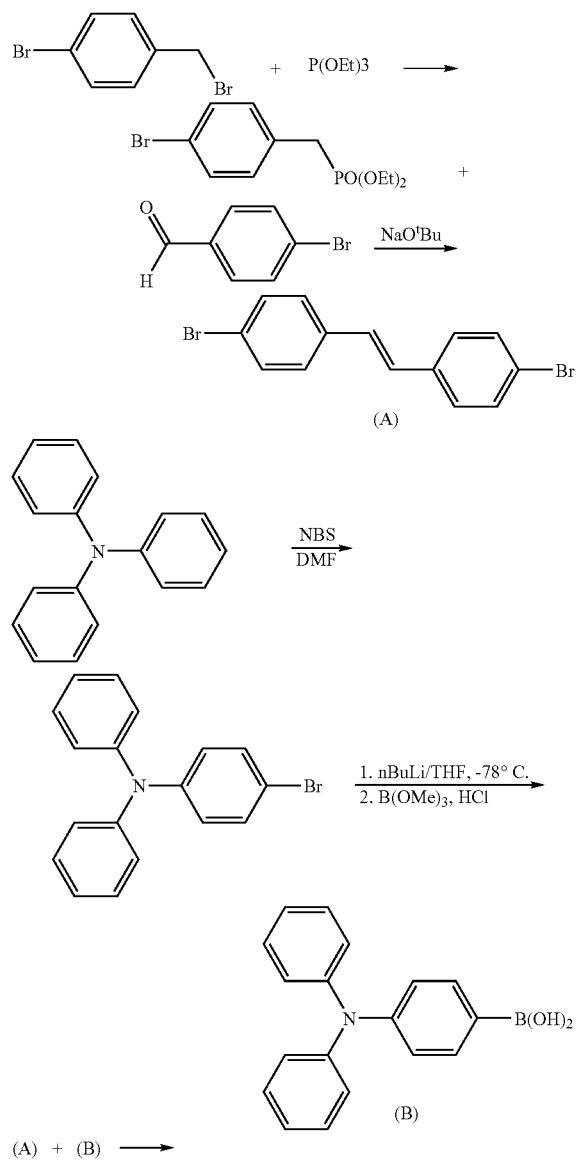

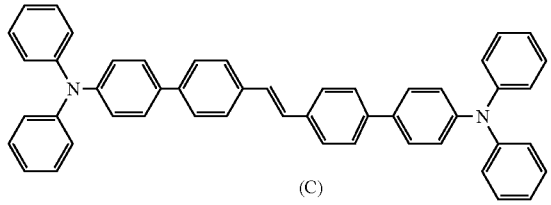

The results of a $^1$H-NMR (CDCl$_3$, 400 MHz) analysis of compound are (C) are δ=7.59 (s, 4H); 7.52 (d, 2H); 7.3 (t, 4H); 7.16 (t, 7H); 7.05 (t, 2H). The melting point of compound (C) is 242° C., and the glass transition point of compound (C) is 105° C. The results of an elemental analysis are as follows. The values in the parentheses are theoretical values.

C: 90.13% (90.09%)

H: 5.75% (5.71%)

EXAMPLE 2

This example illustrates the manufacturing of the organic EL device according to the embodiment of this invention.

First, a 100 mm×100 mm glass substrate is provided, wherein an ITO layer with a thickness of 150 nm is formed on the glass substrate. After photolithography and etch processes, a pattern of 10 mm×10 mm emitting region is formed. In the condition of 10$^{-5}$ Pa, a hole transporting material, such as TPD or NPB (N,N'-diphenyl-N,N'-bis-(1-naphthalenyl)-[1,1'-biphenyl]-4,4'-diamine), is formed on the glass substrate utilizing the evaporation method. In this case, the evaporation ratio of the hole transporting material is maintained at 0.2 nm/sec. The formulas of TPD and NPB are as follows:

TPD:

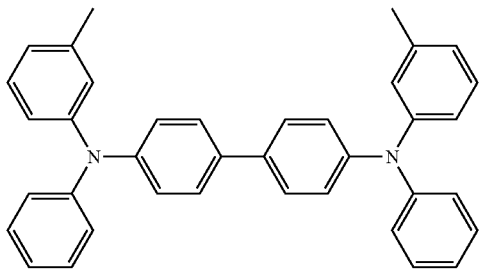

NPB:

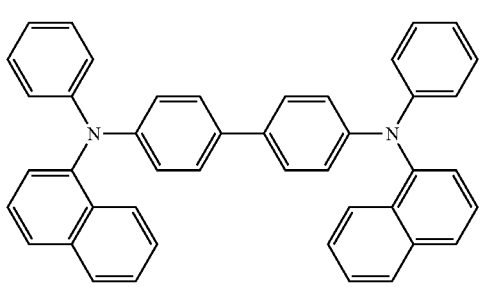

Next, an organic EL material of the compound (C) is formed on the hole transporting material as a luminescent layer. The thickness of the luminescent layer is about 45 nm, and the evaporation ratio of the organic EL material is maintained at 0.2 nm/sec.

Then, AlQ3 (tris(8-quinolino)aluminum) of the following formula is formed on the luminescent layer as an electron transporting layer. The thickness of the electron transporting layer is about 20 nm, and the evaporation ratio of AlQ3 is 0.2 nm/sec.

AlQ3:

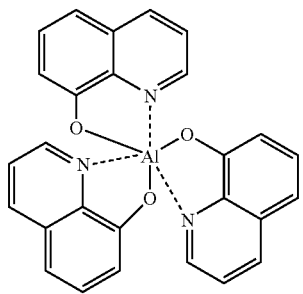

Finally, lithium fluoride (LiF) and aluminun (Al) are formed on the electron transporting layer as a cathode, and have a thickness of 1.2 nm and 150 nm, respectively. Following the steps, an organic EL device according to an embodiment of this invention is completed.

Figure 2:
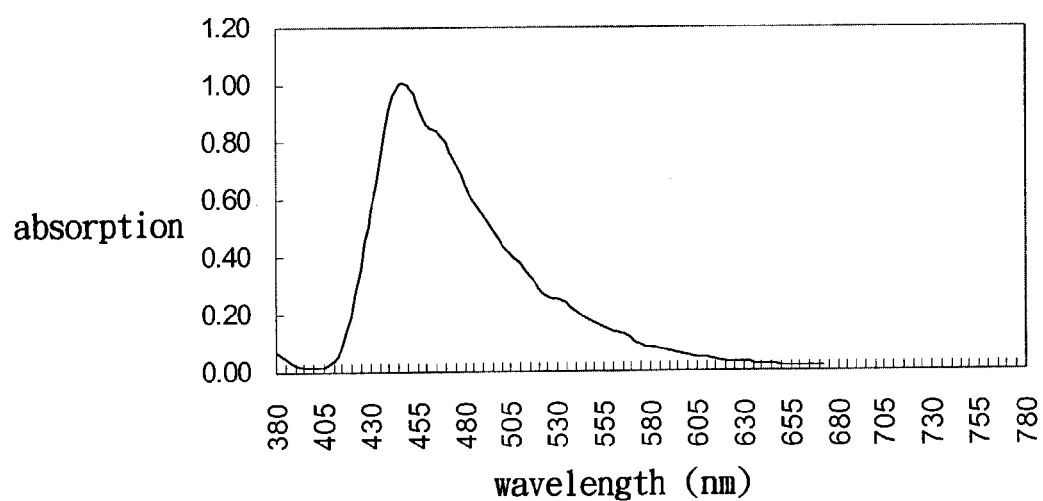
FIG. 2 is a coordinate figure showing EL spectrum of an EL device according to an embodiment of the invention.
Figure 3:
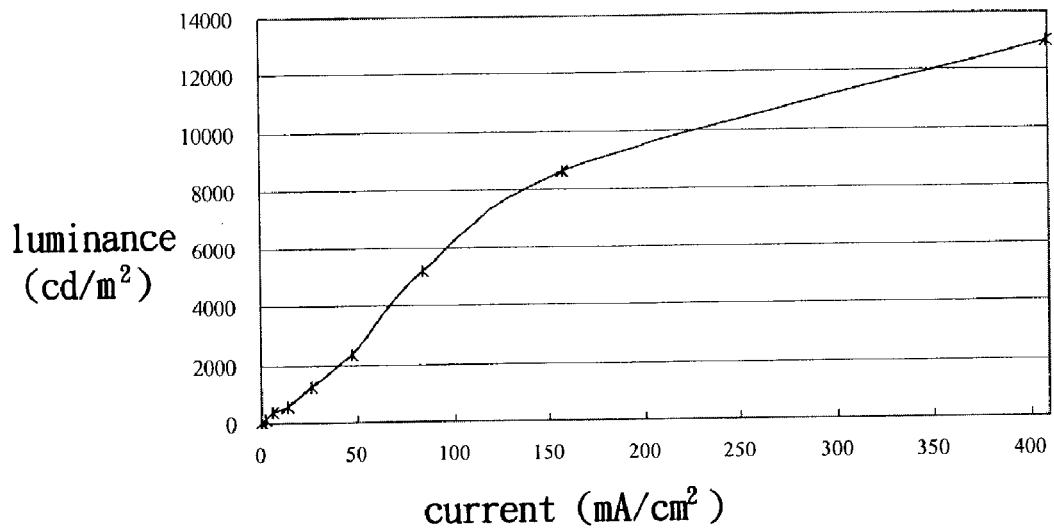
FIG. 3 is a coordinate figure showing current vs. luminance (I-B) according to the embodiment of the invention.
Figure 4:
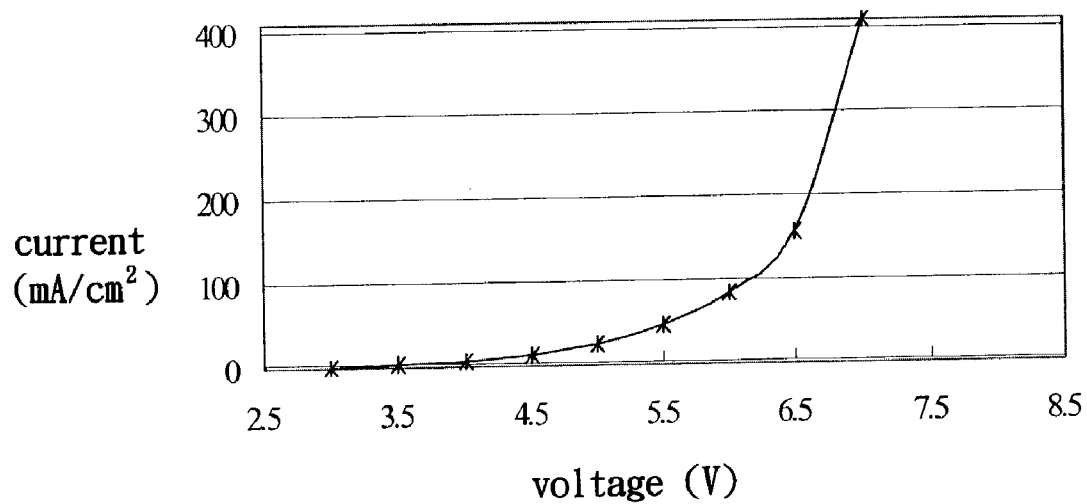
FIG. 4 is a coordinate figure showing current vs. voltage (I-V) according to the embodiment of the invention.

In this case, the luminescent qualities of the organic EL device according to the embodiment are measured with direct current using Keithly 2000. Then, the organic EL device emitting blue light is obtained. Furthermore, the EL spectrum of the organic EL device is measured using a spectrum meter manufactured by Otsuka Electronic Co., wherein the detector is a photodiode array. In this case, the EL spectrum is shown in FIG. 2, and a luminescent wavelength of 455 nm is obtained. The FIGS. 3 and 4 illuminate, respectively, a current vs. luminance (I-B) curve and a current vs. voltage (I-V) curve of the organic EL device according to the embodiment of the invention. Consequently, when 6 volts are applied, the luminance of the organic EL device is 5180 cd/m$^2$, the current density is 83 mA/cm$^2$, the efficiency is 3.88 lm/W or 6.2 cd/A, and the C.I.E. chromaticity coordinates are (X 0.17, Y 0.17).

EXAMPLE 3

This example compares the organic EL material according to an embodiment of this invention with conventional organic EL materials.

A conventional organic EL material is represented by the following formula (II):

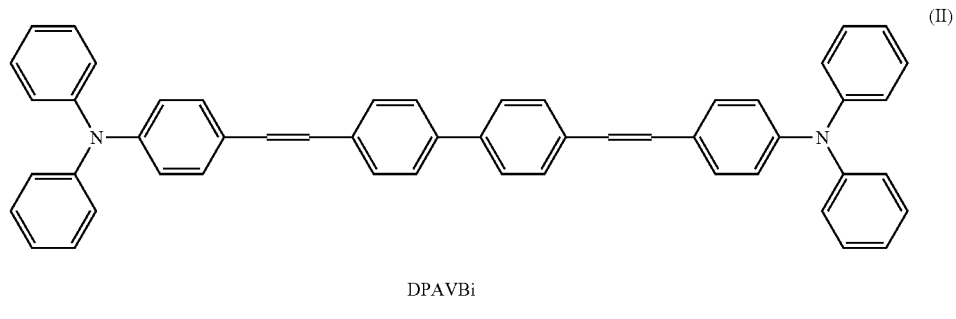

DPAVBi

In this prior art, when the organic EL material of formula (II) is utilized to form a luminescent layer of a conventional organic EL device, the luminance of this organic EL device is 1660 cd/m$^2$, the current density is 71 mA/cm$^2$, the efficiency is 1.84 lm/W or 2.34 cd/A, and the C.I.E. chromaticity coordinates are (X 0.15, Y 0.20) while 6 volts are applied.

Another conventional organic EL material is represented by the following formula (III):

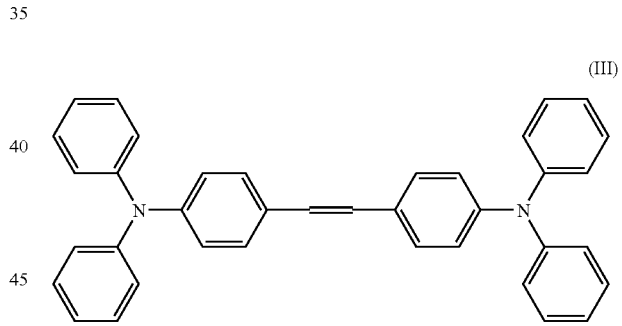

When the organic EL material of formula (III) is utilized to form a luminescent layer of a conventional organic EL device, the luminance of this organic EL device is 1550 cd/m$^2$, the current density is 45 mA/cm$^2$, the efficiency is 1.25 lm/W or 2.7 cd/A, and the C.I.E. chromaticity coordinates are (X 0.14, Y 0.16) while 6 volts are applied.

It is obvious that the organic EL device having the organic EL material of formula (I) is better than that having the organic EL material of formula (II) or (III) both in maximum luminance and luminous efficiency.

In addition, the organic EL material of formula (I) according to this invention is a symmetric compound, so that it has a higher glass transition temperature. Therefore, thermal degradation of the organic EL material of formula (I) during manufacturing processes would not easily occur. In other words, the organic EL material of formula (I) has an improved thermal stability.

In summary, the organic EL material and organic EL device of the presented invention can improve luminance, emitting efficiency, driving voltage, color impurity, and thermal stability.

While the invention has been described by way of example and in terms of the preferred embodiment, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

The invention claimed is:

1. An organic electroluminescent material of the formula:

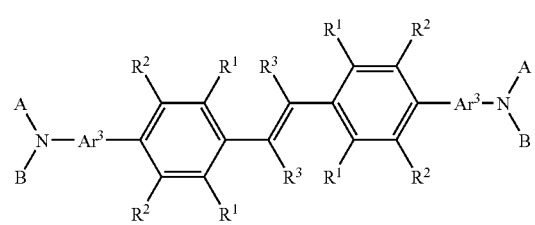

wherein $R^1$, $R^2$ and $R^3$ are at least one selected from the group consisting of hydrogen, halogen, nitryl, alkyl, cycloalkyl, alkyloxy, alkenyl, amine, aryl, polyaryl, arylalkyl, and propenyloxy, $Ar^3$ is at least one selected from the group consisting of unsubstituted or substituted aryl having 6 to 30 carbon atoms and unsubstituted or substituted polyaryl having 6 to 30 carbon atoms, and A is at least one selected from the group consisting of alkyl, cycloalkyl, alkyloxy, alkenyl, amine, aryl, polyaryl, arylalkyl, and propenyloxy, B is at least one selected from the group consisting of hydrogen, alkyl, cycloalkyl, alkyloxy, alkenyl, amine, aryl, polyaryl, arylalkyl, and propenyloxy, wherein $Ar^3$ bonds with A.

2. The organic electroluminescent material of claim 1, wherein $R^1$, $R^2$ and $R^3$ are at least one selected from the substituted or unsubstituted group consisting of alkyl having 1 to 10 carbon atoms, cycloalkyl having 1 to 10 carbon atoms, alkyloxy having 1 to 10 carbon atoms, alkenyl having 1 to 10 carbon atoms, amine, aryl having 6 to 30 carbon atoms, polyaryl having 6 to 30 carbon atoms, arylalkyl having 6 to 30 carbon atoms, and propenyloxy having 1 to 10 carbon atoms.

3. The organic electroluminescent material of claim 1, wherein $Ar^3$ is at least one selected from the group consisting of

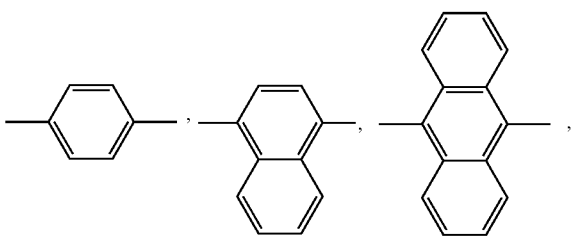

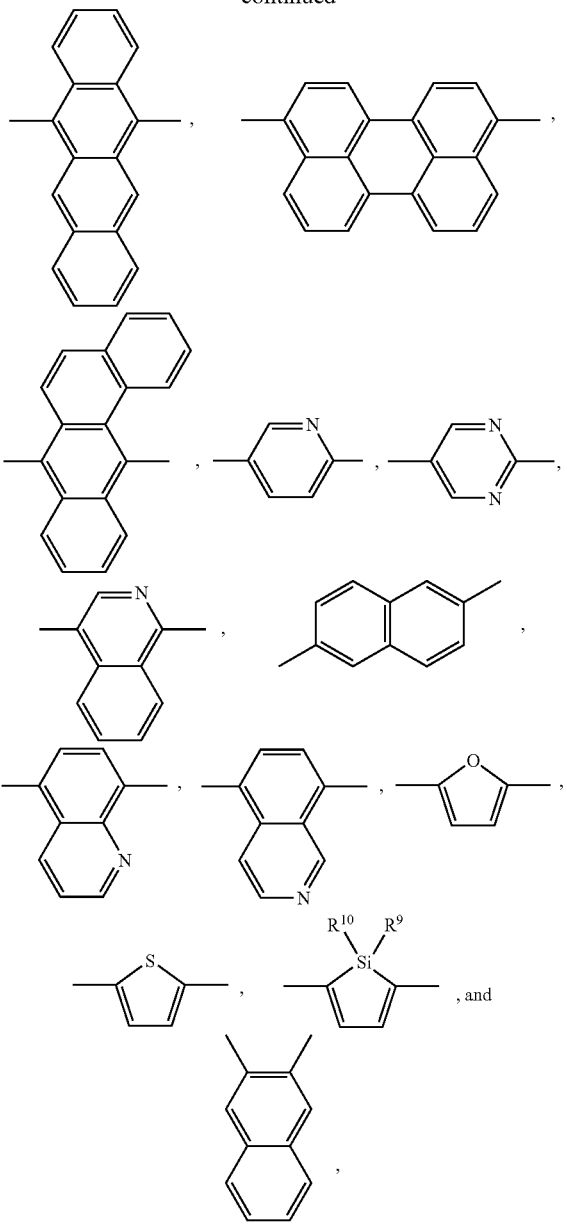

wherein, $R^9$ and $R^{10}$ are at least one selected from the substituted or unsubstituted group consisting of alkyl having 1 to 10 carbon atoms, aryl having 6 to 30 carbon atoms, polyaryl having 6 to 30 carbon atoms, and arylalkyl having 6 to 30 carbon atoms.

4. The organic electroluminescent material of claim 1, wherein A and B are at least one selected from the substituted or unsubstituted group consisting of alkyl having 1 to 10 carbon atoms, cycloalkyl having 1 to 10 carbon atoms, alkyloxy having 1 to 10 carbon atoms, alkenyl having 1 to 10 carbon atoms, amine, aryl having 6 to 30 carbon atoms, polyaryl having 6 to 30 carbon atoms, arylalkyl having 6 to 30 carbon atoms, and propenyloxy having 1 to 10 carbon atoms.

5. An organic electroluminescent device comprising two electrodes and at least one organic electroluminescent layer sandwiched between the electrodes, wherein the organic electroluminescent layer comprises an organic electroluminescent material of the formula:

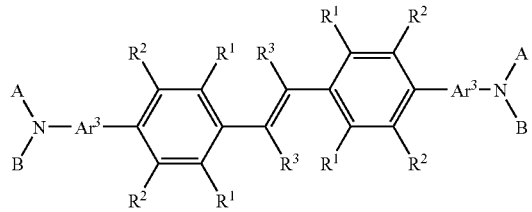

wherein $R^1$, $R^2$ and $R^3$ are at least one selected from the group consisting of hydrogen, halogen, nitryl, alkyl, cycloalkyl, alkyloxy, alkenyl, amine, aryl, polyaryl, arylalkyl, and propenyloxy, $Ar^3$ is at least one selected from the group consisting of aryl and polyaryl, and A is at least one selected from the group consisting of alkyl, cycloalkyl, alkyloxy, alkenyl, amine, aryl, polyaryl, arylalkyl, and propenyloxy, B is at least one selected from the group consisting of hydrogen, alkyl, cycloalkyl, alkyloxy, alkenyl, amine, aryl, polyaryl arylalkyl, and propenyloxy, wherein $Ar^3$ bonds with A.

6. The device of claim 5, wherein $R^1$ and $R^2$ are at least one selected from the substituted or unsubstituted group consisting of alkyl having 1 to 10 carbon atoms, cycloalkyl having 1 to 10 carbon atoms, alkyloxy having 1 to 10 carbon atoms, alkenyl having 1 to 10 carbon atoms, amine, aryl having 6 to 30 carbon atoms, polyaryl having 6 to 30 carbon atoms, arylalkyl having 6 to 30 carbon atoms, and propenyloxy having 1 to 10 carbon atoms, $R^3$ is at least one selected from the substituted or unsubstituted group consisting of alkyl having 1 to 10 carbon atoms, cycloalkyl having 1 to 10 carbon atoms, alkyloxy having 1 to 10 carbon atoms, alkenyl having 1 to 10 carbon atoms, amine, aryl having 6 to 30 carbon atoms, arylalkyl having 6 to 30 carbon atoms, and propenyloxy having 1 to 10 carbon atoms.

7. The device of claim 5, wherein $Ar^3$ is at least one selected from the substituted or unsubstituted group consisting of aryl having 6 to 30 carbon atoms, and polyaryl having 6 to 30 carbon atoms.

8. The device of claim 7, wherein A is at least one selected from the group consisting of alkyl, cycloalkyl, alkyloxy, alkenyl, amine, aryl, polyaryl, and propenyloxy, and $Ar^3$ bonds with A.

9. The device of claim 7, wherein B is at least one selected from the group consisting of alkyl, cycloalkyl, alkyloxy, alkenyl, amine, aryl, polyaryl, arylalkyl, and propenyloxy, and $Ar^3$ bonds with B.

10. The device of claim 7, wherein $Ar^3$ is at least one selected from the group consisting of

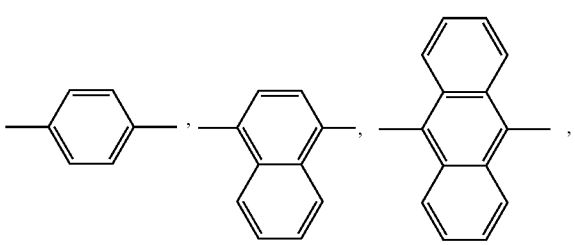

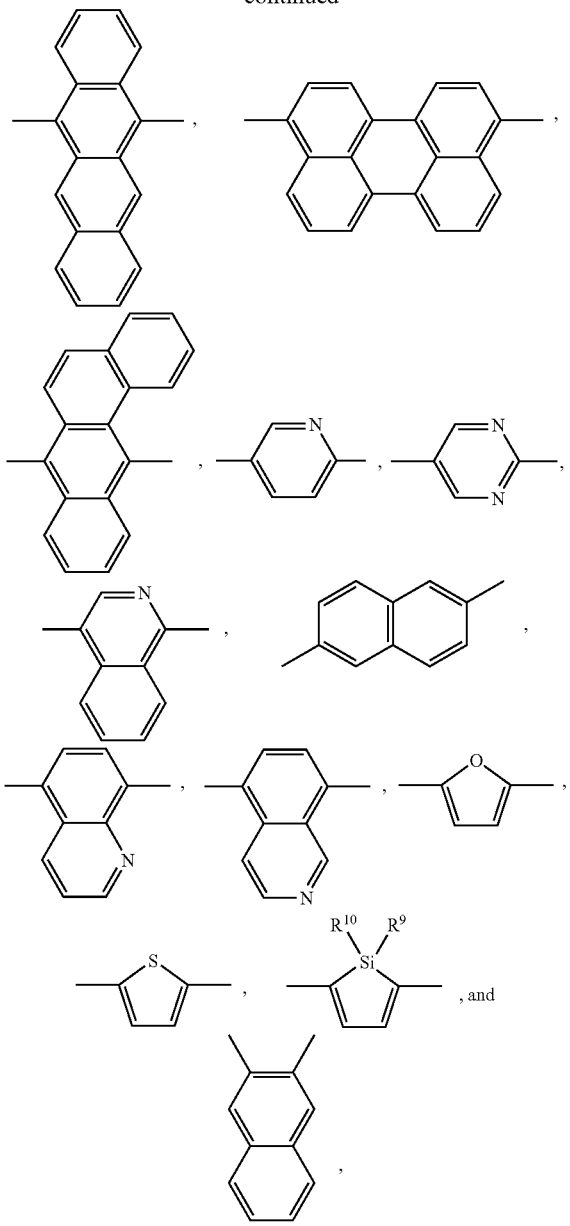

wherein, $R^9$ and $R^{10}$ are at least one selected from the substituted or unsubstituted group consisting of alkyl having 1 to 10 carbon atoms, aryl having 6 to 30 carbon atoms, polyaryl having 6 to 30 carbon atoms, and arylalkyl having 6 to 30 carbon atoms.

11. The device of claim 5, wherein A and B are at least one selected from the substituted or unsubstituted group consisting of alkyl having 1 to 10 carbon atoms, cycloalkyl having 1 to 10 carbon atoms, alkyloxy having 1 to 10 carbon atoms, alkenyl having 1 to 10 carbon atoms, amine, aryl having 6 to 30 carbon atoms, polyaryl having 6 to 30 carbon atoms, arylalkyl having 6 to 30 carbon atoms, and propenyloxy having 1 to 10 carbon atoms.

12. The device of claim 5, wherein the organic electroluminescent layer further comprises an aryl amino compound.

13. The device of claim 12, wherein the aryl amino compound is substituted with aryl group.

14. The device of claim 12, wherein the aryl amino compound is substituted with polyaryl group.

15. The device of claim 12, wherein the glass transition temperature of the organic electroluminescent layer is higher than 100° C.

16. The device of claim 5, wherein the organic electroluminescent material is doped in the organic electroluminescent layer.

17. The device of claim 16, wherein the doping ratio of the organic electroluminescent material is greater than 0.01 wt %.

18. The device of claim 16, wherein the doping ratio of the organic electroluminescent material is less than 10 wt %.

19. The device of claim 5, wherein the organic electroluminescent material is doped in a hole transporting layer of the organic electroluminescent layer.

20. An organic electroluminescent material of the formula:

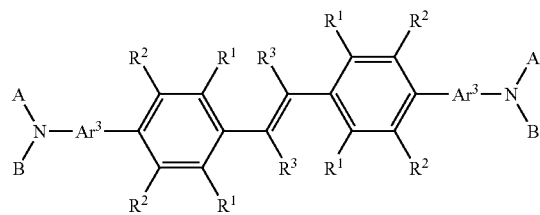

wherein $R^1$, $R^2$ and $R^3$ are at least one selected from the group consisting of hydrogen, halogen, nitryl, alkyl, cycloalkyl, alkyloxy, alkenyl, amine, aryl, polyaryl, arylalkyl, and propenyloxy, $Ar^3$ is at least one selected from the group consisting of unsubstituted or substituted aryl having 6 to 30 carbon atoms and unsubstituted or substituted polyaryl having 6 to 30 carbon atoms, and A and B are at least one selected from the group consisting of alkyl, cycloalkyl, alkyloxy, alkenyl, amine, aryl, polyaryl, arylalkyl, and propenyloxy, wherein $Ar^3$ bonds with A and B.

* * * * *